United States Patent [19]

Martinsson et al.

[11] 3,972,855

[45] Aug. 3, 1976

[54] QUATERNARY AMMONIUM COMPOUNDS AND TREATMENT OF PLASTIC AND OTHER MATERIALS THEREWITH

[75] Inventors: Eva Margareta Martinsson, Stenungsund; Karl Martin Edvin Hellsten, Odsmal, both of Sweden

[73] Assignee: Modokemi Aktiebolag, Stenungsund, Sweden

[22] Filed: Dec. 10, 1973

[21] Appl. No.: 423,592

Related U.S. Application Data

[63] Continuation-in-part of Ser. No. 306,251, Nov. 10, 1972, abandoned.

[52] U.S. Cl. .......................... 260/567.6 M; 252/8.9

[51] Int. Cl.[2] .......................................... C07C 93/04

[58] Field of Search .................. 260/567.6, 567.6 M

[56] References Cited

UNITED STATES PATENTS

| | | | |
|---|---|---|---|
| 3,326,927 | 6/1967 | Aamoth | 260/567.6 M |
| 3,445,440 | 5/1969 | Susi et al. | 260/567.6 M |
| 3,624,082 | 11/1971 | Skokie et al. | 260/567.6 M |

FOREIGN PATENTS OR APPLICATIONS

| | | | |
|---|---|---|---|
| 1,034,042 | 6/1966 | United Kingdom | 260/567.6 |

OTHER PUBLICATIONS

Gaylord et al., "Polyethers," Interscience Publishers Inc., N.Y., (1963), pp. 106–107.

*Primary Examiner*—James O. Thomas, Jr.
*Assistant Examiner*—James H. Reamer

[57] ABSTRACT

Quaternary ammonium compounds are provided which are useful in the treatment of substrates such as plastic materials and textile materials, both woven and nonwoven, from natural and synthetic fibers and mixtures thereof, to impart antistatic properties.

A process is also provided for the preparation of such compounds, and for the treatment of substrates with such compounds.

6 Claims, No Drawings

QUATERNARY AMMONIUM COMPOUNDS AND TREATMENT OF PLASTIC AND OTHER MATERIALS THEREWITH

This application is a continuation-in-part of Ser. No. 306,251, filed Nov. 10, 1972 and now abandoned.

U.S. Pat. No. 3,395,708 and Reissue No. 26,939 to Hervey and George dated Aug. 6, 1968 and Aug. 18, 1970 and French Pat. No. 1,265,818 disclose that treatment of unfiberized wet cellulose pulp with a surfactant before or during the formation of the cellulose pulp on a drying machine or on a paper machine reduces the interfiber bonds of the cellulose. The improvement is accomplished by impregnating a wet slurry of wood pulp with a cationic debonding agent, forming the wet slurry into a wet pressed wood pulp sheet, and mechanically fiberizing the dried sheet to form a substantially completely fiberized fluffed fibrous wood pulp batt. The result of this treatment is a cellulose batt, sheet or paper having improved softness and a low degree of mechanical strength. Among the surfactants said to be useful in this way are long chain cationic surfactants, preferably with at least twelve carbon atoms in at least one alkyl chain, and illustrative, but non-limiting, specific examples of same are fatty dialkyl amine quaternary salts, mono fatty alkyl tertiary amine salts, primary amine salts, and unsaturated fatty alkyl amine salts.

The hydrophilic cationic portion of the surfactant is considered to be attracted to the negatively-charged cellulose fibers, while the hydrophobic portions of the molecule are exposed on the surface, thus rendering the surface of the fibers hydrophobic. The interbonds between the cellulose fibers are reduced, and the defibration into cellulose fluff is thereby facilitated. However, a highly hydrophilic cellulose pulp when treated with such cationic surfactants will exhibit more hydrophobic properties than the corresponding untreated cellulose pulp. If the cellulose pulp or paper is intended to be used in the production of highly absorbent products, such as sanitary products, hydrophobicity is not desirable, since it reduces absorptivity. Consequently, in the treatment of such cellulose derivatives, it has been necessary in order to improve the wettability of the cellulose fibers after the treatment to add a wetting agent, which is preferably added to the cellulose pulp sheet in a separate operation, owing to the low degree of affinity to cellulose of these wetting agents.

Tobler et al. U.S. Pat. No. 3,636,114 dated Jan. 18, 1972 describes tertiary amines and quaternary ammonium compounds and a method for preparing such amines and quaternary ammonium compounds. The quaternary ammonium compounds have the formula:

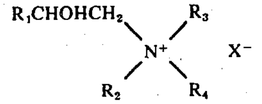

wherein $R_1$ is alkyl, aryl, aralkyl or alkaryl, and $R_2$ is alkyl, aralkyl, alkaryl, 2-hydroxy alkyl, 1-alkoxymethyl, and $R_1CHOHCH_2$; $R_3$ and $R_4$ are lower alkyl, $HOCH_2CH_2$ or $HO-CH_2CH_2CH_2$; and X is a hydroxyl or salt-forming anion. These quaternary ammonium compounds are prepared from tertiary amines of the formula:

$$(R_1[OCH_2]_nCHOHCHR_5)_2NR_3$$

These compounds are said to have utility as fabric softening agents and as anti-bacterial compounds or germicides. There is no indication that such compounds will impart antistatic properties to fabrics or other substrates. Neither is there any disclosure of oxyalkylene groups containing more than one carbon atom per unit.

In accordance with the invention, it has been determined that bis(alkoxy(2-hydroxy)propylene) quaternary ammonium compounds which contain both cationic and nonionic hydrophilic groups when used to treat textile materials impart improved antistatic properties and/or softness while at the same time preserving good hydrophilic properties. The quaternary ammonium compounds in accordance with the invention have the general formula:

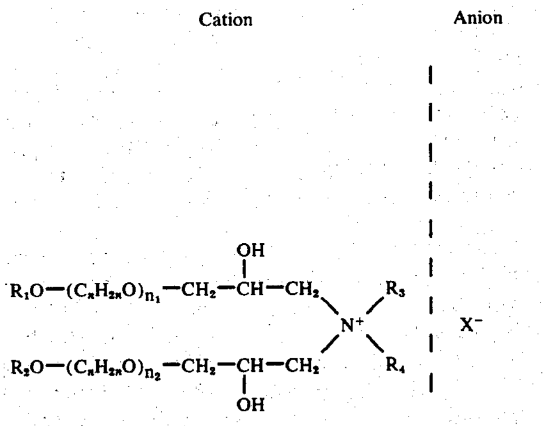

In this formula:

$R_1$ and $R_2$ are aliphatic hydrocarbon groups, which can be either saturated or unsaturated, having from about eight to about twenty-two carbon atoms;

$R_3$ and $R_4$ are methyl, ethyl or hydroxyethyl;

$n$ is a number from 2 to 4, representing the number of carbon atoms in the oxyalkylene substituent, which can thus be oxyethylene, oxypropylene-1,2 or -1,3 or oxybutylene-1,2 -1,3, -1,4 or -2,3;

$n_1$ and $n_2$ are numbers within the range from 0.5 to about 10, representing the number of oxyalkylene groups present in each substituent; $n_1$ and $n_2$ usually represent average values, and therefore need not be integers. When $n_1$ and/or $n_2$ are less than one, they represent an average of molecules having zero and one or more oxyalkylene groups; and X is a salt-forming anion.

The quaternary ammonium compounds in accordance with the invention impart superior antistatic properties to substrates than the alkyl quaternary ammonium compounds heretofore used, such as those of U.S. Pat. No. 3,395,708. The improvement in antistatic properties is believed due to the presence of the 2-hydroxy-oxypropylene group and the oxyalkylene groups. Compounds having from one to two oxyalkylene groups and one 2-hydroxy-oxypropylene group impart the best antistatic properties, and are therefore preferred. In these compounds, $n_1$ and $n_2$ are numbers within the range from 0.5 to 2.

Quaternary ammonium compounds falling within the above formula in which $R_1$ and $R_2$ have from about eight to about fourteen carbon atoms are freeze-thaw stable in aqueous solutions at concentrations of from about 5% to about 10%; that is, at these concentrations they have no or only a slight tendency to gel and freeze-separate when subjected to repeated freezing and thawing. In concentrated or pure form, these compounds are liquids, which facilitates their formulation into consumer products.

The quaternary compounds in accordance with the invention can be applied to the substrate in the form of solids, such as powders or pastes, or as solutions, in water or in an organic solvent. In such solutions, the concentration of quaternary ammonium compound can range from about 0.01 to about 25%, preferably from about 0.1 to about 10%.

In the case of solutions for application to textile materials, the concentration of the quaternary ammonium compound can be within the range from about 0.01 to about 0.05 gram, and preferably from about 0.05 to about 0.15 gram, per liter of solution. Aqueous solutions of such concentrations are quite useful, for example, as rinsing solutions at any of the stages of textile processing during which aqueous rinsing solutions are used. Due to their good affinity for textile fibers, the quaternary ammonium compounds can be introduced into any rinsing solution in the course of the process, but the best and most lasting effect is obtained if the quaternary ammonium compound is included in the last rinsing solution.

The compounds can also be added at the prewash or in the main wash operations, but in these cases the antistatic effects may be less per unit weight of compound applied to the textile material, probably because of losses of the compound during later processing.

The usual solvent used is water. However, if rapid volatilization of the solvent is desired, the quaternary ammonium compounds of the invention can be applied from a solution in a rapidly volatilizable organic solvent, such as acetone, methanol, ethanol, isopropanol, or mixtures thereof. In this case, the concentrations are the same as aqueous solutions, within the range from about 5% to about 10% by weight of the quaternary ammonium compound.

The solutions of the quaternary ammonium compounds of the invention can also be applied by dipping, spraying, or coating, using conventional techniques. This sort of application is useful on textile materials which normally are very seldom washed, or are not washed at all, or on leather or plastic sheet material, or on plastic films coated on other base such as wood. When applied in this way, the composition usually contains the quaternary ammonium compound in a concentration within the range from about 5% to about 10%.

The application solution can also include nonionic surfactants, such as adducts of ethylene oxide or propylene oxide and aliphatic alcohols or alkyl phenols, to improve the rewettability of the treated material. Solubility-enhancing additives, such as the monoethyl ether of diethylene glycol, can also be added.

The quaternary ammonium compounds of the invention are applied to the substrate in an amount within the range from about 0.001% to about 2% by weight of the substrate.

The compounds of the invention impart antistatic properties to textile materials of all kinds including both woven and nonwoven materials made of natural or synthetic fibers or mixtures thereof, such as, for example, rayon, acetate rayon, cellulose acetate-propionate, cellulose acetate-butyrate, polyvinyl chloride, polyamide, polypropylene, polyethylene, polyacrylonitrile, polyesters such as ethylene glycol-terephthalic acid polymers, cotton, linen, jute, ramie, sisal, wool, mohair, alginate fibers, zein fibers, glass, potassium titanate, bast, bagasse, polyvinylidene chloride, and fur fibers of various kinds such as beaver, rabbit, seal, muskrat, otter, mink, caracul, lamb and squirrel.

The textile materials can take any form, including nonwoven materials such as felts, bats and mats; woven materials such as fabrics, cloth, carpets, rugs and upholstery; synthetic fur materials; curtains, and covering materials of all kinds.

The compounds of the invention are applicable to impart antistatic properties to leather materials, such as leather furniture and leather clothing.

They are also applicable to plastic surfaces, many of which have a pronounced tendency to develop a static charge, such as synthetic phonograph records which are usually made of polyvinyl chloride; to painted, varnished and lacquered surfaces which bear a synthetic resinous coating film; to metal foils, and chassis for electric and electronic devices, such as radios, hi-fis, phonograph systems, sound amplification systems, amplifiers, television, and sound-recording equipment.

The synthesis of the alkoxy-2-hydroxy-propylene quaternary ammonium compounds in accordance with the invention includes the following reaction steps:

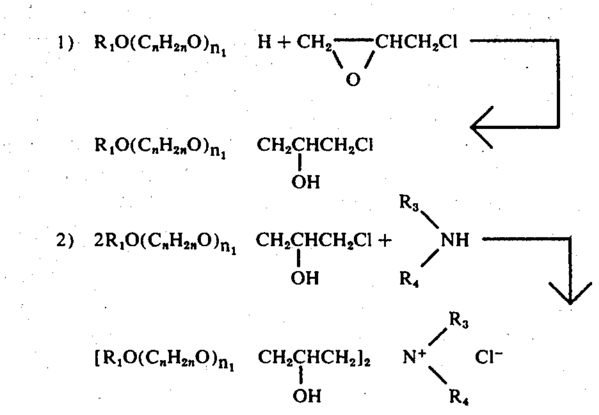

In the above reaction formulae, $R_1$, $R_3$, $R_4$, $n$ and $n_1$ have the meanings earlier mentioned.

The alkoxyalkylene oxy-(2-hydroxy)propylene quaternary ammonium compounds in accordance with the invention can be prepared by reaction of from 1 to about 10 mols of ethylene oxide with one mol of an aliphatic alcohol having from about eight to about twenty-two carbon atoms. The reaction of alkylene oxide with the alcohol is carried out in the presence of an alkali catalyst, preferably sodium hydroxide, at an elevated temperature. If no oxyalkylene unit is present, of course this reaction step is omitted.

The resulting alkoxy glycol ether is reacted with epichlorhydrin, producing the corresponding chloroglyceryl or chlorohydroxypropylene ether, which is then reacted with a secondary amine having the formula $R_3R_4NH$, where $R_3$ and $R_4$ are methyl, ethyl, or hydroxyethyl. The product is a quaternary ammonium compound of the invention, in the form of its chloride salt. The chloride ion can then be exchanged by another ion, using known techniques, for example, by addition of a sodium salt with a higher solubility constant than sodium chloride, or by ion exchange in an anion exchanger. Among anions other than chloride ion which can serve as X in the quaternary ammonium compounds of the invention are nitrate, carbonate, hydroxyl, phosphate, iodide, bromide, methyl sulfate, acetate, carbonate, formate, citrate, propionate, and tartrate. The monovalent anions are preferred.

The reaction between the alkylene oxide adduct and the epichlorhydrin proceeds at an elevated temperature within the range from about 100° to about 150°C in the presence of a catalyst, such as stannic chloride, boron trifluoride, and perchloric acid, $HClO_4$. These give a rapid easily controllable reaction, but other acid catalysts such as toluene sulfonic acid and sulfuric acid can also be used.

In order to ensure complete reaction of the alkylene oxide adduct, an excess of epichlorhydrin is generally added.

The quaternization of the secondary amine with the chloroglyceryl ether is carried out in the presence of alkali, generally sodium hydroxide, at an elevated temperature within the range from about 100° to about 150°C. The reaction is carried out in the presence of an organic solvent with a boiling point of at least 60°C. Suitable organic solvents include methanol, ethanol, and the monoethylether of diethylene glycol.

It is also possible to react the chloroglyceryl ether with ammonia or with a primary amine having a methyl, ethyl, or hydroxyethyl group, and the resulting product may then be quaternized with methyl or ethyl chloride or dimethyl or diethyl sulfate. However, this procedure is more complicated than the previously described procedure, and it involves more reaction steps, and results in larger amounts of byproducts and lower total yields of the desired quaternary ammonium compounds.

Alkylene oxides which can be used include ethylene oxide; propylene oxide-1,2; propylene oxide-1,3; butylene oxide-1,2; butylene oxide-1,3; butylene oxide-2,3; butylene oxide-1,4.

The aliphatic alcohols having from about eight to about 22 carbon atoms which can be used in the reaction products of the invention include both saturated and unsaturated alcohols, such as octyl alcohol, decyl alcohol, lauryl alcohol, myristyl alcohol, cetyl alcohol, stearyl alcohol, eicosyl alcohol, oleyl alcohol, ricinoleyl alcohol, linoleyl alcohol, and eicosenyl alcohol. The alcohol can also be a mixture of such alcohols, such as are obtained from natural fats and oils by reduction of the fatty acid or fatty acid ester mixtures obtained from such oils, such as coconut oil fatty alcohols, palm oil fatty alcohols, soya oil fatty alcohols, linseed oil fatty alcohols, corn oil fatty alcohols, castor oil fatty alcohols, fish oil fatty alcohols, whale oil fatty alcohols, tallow fatty alcohols, and lard fatty alcohols. Mixtures of synthetic alcohols prepared by the Ziegler procedure or the Oxo process can also be used. Most alcohols manufactured by Oxo process have a branched chain, which makes possible a large number of isomers. The physical properties of these alcohol mixtures are very similar to those of the straight-chain primary alcohols.

Secondary amines which can be used in accordance with the invention include dimethyl amine, diethyl amine, diethanol amine, methyl amine, and methyl hydroxyethyl amine. Primary amines which can be used include methyl amine, ethyl amine, and hydroxyethyl amine.

The following Examples in the opinion of the inventors represent preferred embodiments of their invention.

PREPARATION OF ADDITIVES

Additive A

In a reaction vessel provided with a heating coil, a stirrer, and a reflux condenser for cooling, was placed 300 grams (1 mol) of a melt of tallow fatty alcohol (a mixture of cetyl, stearyl and eicosyl alcohols), which has previously been reacted with 0.5 mol of ethylene oxide per mol of alcohol. The melt was brought to 75°C with stirring, whereupon 3 grams of stannic chloride was introduced, and 101 grams (1.1 mol) epichlorhydrin was then added over 1 hour. After all of the epichlorhydrin had been added, the temperature was increased to 125°C, and held there for a further reaction time of 2 hours. The remaining epichlorhydrin was then removed under vacuum, and the reaction product obtained was 390 grams of a pale yellow viscous liquid.

In an autoclave fitted with a heater and a stirrer was placed 350 grams (0.9 mol) of this reaction product, 125 grams of ethanol, in which 20 grams (0.45 mol) of dimethyl amine had been dissolved, and 23 grams (0.56 mol) of sodium hydroxide dissolved in 15 grams of water. The mixture was held at 125°C in the autoclave for 3 hours. At the conclusion of this time, the unreacted dimethyl amine was removed by bubbling nitrogen gas through the mixture. The rection product was a pale beige substance, having a melting point of 37° to 40°C. Analysis showed that it contained 57% quaternary amine, 10% tertiary amine, 23 grams ethanol, 6% sodium chloride and 4% water, and had the formula:

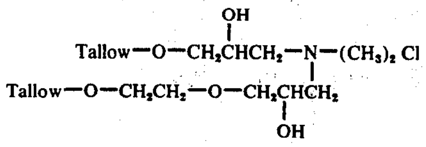

Additive B

Using the above procedure, 2 mols tallow fatty alcohol, 1 mol butylene oxide, 2 mols epichlorhydrin and 1 mol dimethyl amine were reacted to form the product:

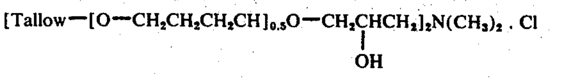

Additive C

Using the above procedure, 2 mols tallow fatty alcohol, 4 mols ethylene oxide, 2 mols epichlorhydrin and 1 mol dimethyl amine were reacted to form the product:

-continued $$[\text{Tallow}-[O-CH_2CH_2]_2O-CH_2\underset{OH}{\underset{|}{C}}HCH_2]_2N(CH_3)_2 \cdot Cl$$

Additive D

Using the above procedure, 2 mols tallow fatty alcohol, 8 mols ethylene oxide, 2 mols epichlorhydrin and 1 mol dimethyl amine were reacted to form the product:

$$[\text{Tallow}-[O-CH_2CH_2]_4O-CH_2\underset{OH}{\underset{|}{C}}HCH_2]_2N(CH_3)_2 \cdot Cl$$

Additive E

Using the above procedure, 2 mols of a mixture $C_{20}$–$C_{22}$ fatty alcohols, 8 mols ethylene oxide, 2 mols epichlorhydrin and 1 mol dimethyl amine were reacted to form the product:

$$[C_{20-22}H_{41-43}[O-CH_2CH_2]_4O-CH_2\underset{OH}{\underset{|}{C}}HCH_2]N(CH_3)_2 \cdot Cl$$

Control I

Using the procedure for Additive A, 2 mols of alcohol, 2 mols epichlorhydrin and 1 mol dimethyl amine were reacted, to form the product:

$$[\text{Cetyl}-OCH_2\underset{OH}{\underset{|}{C}}HCH_2]_2N(CH_3)_2 \cdot Cl$$

Control II

Using the procedure for Additive A, 2 mols of tallow fatty alcohol, 2 mols of epichlorhydrin and 1 mol dimethyl amine were reacted to form the product:

$$[\text{Tallow}-O-CH_2\underset{OH}{\underset{|}{C}}HCH_2]_2N(CH_3)_2 \cdot Cl$$

Additive F

Using the same procedure as in Additive A above, a fatty alcohol mixture (1 mol, 15% decyl alcohol, 47% dodecyl alcohol and 38% tetradecyl alcohol) was reacted with ethylene oxide (1 mol), epichlorhydrin (1.1 mols) and dimethyl amine (0.5 mol), using monoethyl ether of dialkylene glycol as the solvent. The product by analysis contained 57% quaternary ammonium compound in accordance with the invention, having the formula:

$$\left[C_{10-12-14}H_{23-25-27}(OCH_2CH_2)_{0.5}OCH_2\underset{OH}{\underset{|}{C}}HCH_2\right]_2 N(CH_3)_2 \cdot Cl$$

In addition, the reaction mixture contained 2.8% of a tertiary amine containing an alkyl ether group and two methyl groups and 25% monoethyl ether of diethylene glycol. The remainder was water, sodium chloride, and unreacted starting material. The product mixture had a softening point of 12°C, became clear at 33°C, and when allowed to cool had a hardening point of 10°C.

Twelve parts by weight of this reaction product was dissolved in 88 parts by weight of water. The resulting solution was liquid at room temperature; it became solid at 0°C. When cooled further, so that the water solution was frozen, and then thawed, no tendency towards gelation was noted.

EXAMPLES 1 to 5

The antistatic properties of Additives A to E above were evaluated in comparison with Arquad 2 HT 75, distearyl dimethyl ammonium chloride, and Controls I and II, above, using a sequence of washing tests in a drum washing machine and test swatches of nylon cloth as the textile material. The test swatches were washed with the same commercial nonsoap detergent in each test, at 22°C. In the last rinsing water, a solution of one of the additives was used in an amount corresponding to 0.5 gram per kilogram of nylon. After treatment, the time required for discharge of half the electric charge applied to the nylon in a Rothschild Static Voltmeter R-1020 was determined. The following results were obtained:

TABLE I

| Example No. | Additive | Half-life (seconds) |
|---|---|---|
| Control | Commercial product | 12 |
| Control I | | 10 |
| Control II | | 10 |
| 1 | A | 6 |
| 2 | B | 6 |
| 3 | C | 5 |
| 4 | D | 6 |
| 5 | E | 6 |

It is apparent from the above results that while Controls I and II, which do not contain oxyethylene units, have better antistatic properties than the commercial additive, the addition of oxyethylene units improved (Additives A, B, C, D and E) the anti-static effect so that the half-life for the nylon swatches treated with these additives is half or less that for the commercial additive.

It is apparent from these data that the quaternary ammonium compounds in accordance with the invention have a better antistatic effect than the closely-related quaternary ammonium compounds of the prior art. It is further evident that the compounds wherein $n_1$ and $n_2$ are within the range from 0.2 to 2 have a superior antistatic effect.

EXAMPLE 6

The antistatic properties of Additive F were evaluated against distearyl dimethyl ammonium chloride, Arquad 2 HT 75, for comparison. Test swatches of cotton terry cloth were washed with commercial nonsoap detergent at 90°C in a drum washing machine. The last rinsing water contained either the Additive F or the distearyl dimethyl ammonium chloride, applying 1.2 grams of dry additive per kilogram of cotton terry cloth swatches. This washing cycle was repeated five times.

The water absorptivity of the treated terry cloth swatches was determined by pressing a circular testing piece against the upper surface of a glass fiber plate while the entire undersurface was in contact with water. By measuring the decrease in the amount of water as a function of time, the water absorption was determined. The following results were obtained:

TABLE II

| | Water Absorption ml of water/g cloth absorbed after 50 secs. |
|---|---|
| Untreated terry cloth | 3.1 |
| Terry cloth treated with 1.2 g/kg of distearyl dimethyl ammonium chloride | 1.1 |
| Terry cloth treated with 1.2 g/kg of the cation surfactant according to the invention | 2.4 |

Antistatic properties were evaluated on nylon cloth swatches which had been washed at 20°C, using a non-soap synthetic detergent with the additive in accordance with the invention added to the last rinse in the same manner as in Examples 1 to 5. After conditioning the nylon swatches for 24 hours at a relative humidity of 65% and 20°C, the time required for discharge of half the electric charge applied to the nylon in a Rothschild Static Voltmeter R-1020 was determined. A strip of the cloth was stretched between two metal clips, to which a potential of 100 volts was applied. The following results were obtained:

TABLE III

| Product | Half-life (seconds)[1] |
|---|---|
| Untreated nylon cloth | 74 |
| Nylon cloth treated with 1.2 g/kg of distearyl dimethyl ammonium chloride | 34 |
| Nylon cloth treated with 1.2 g/kg of the cation surfactant according to the invention | 9 |

[1] Due to different testing conditions, no direct comparison with the results from Examples 1 to 5 can be made.

The above data show that this compound is a liquid at room temperature, and forms a freeze-thaw-stable aqueous solution at a concentration of 12%. Compared to distearyl dimethyl ammonium chloride, the quaternary ammonium compound according to the invention imparts softening, antistatic and water-absorption effects to the textile material treated.

Having regard to the foregoing disclosure, the following is claimed as the inventive and patentable embodiments thereof:

1. Quaternary ammonium compounds capable of imparting excellent antistatic properties to a substrate, having the general formula:

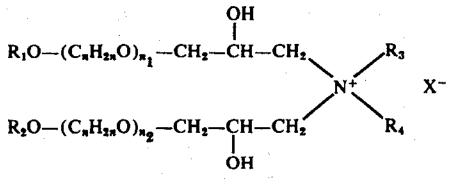

wherein:

$R_1$ and $R_2$ are aliphatic hydrocarbon groups, having from about eight to about 22 carbon atoms;

$R_3$ and $R_4$ are methyl, ethyl or hydroxyethyl;

$n$ is a number from 2 to 4, representing the number of carbon atoms in the oxyalkylene substituent;

$n_1$ and $n_2$ are numbers within the range from 0.5 to about 10, representing the number of oxyalkylene groups present in each substituent; and represent average values; and X is an anion selected from the group consisting of chloride, bromide, iodide, nitrate, hydroxyl, phosphate, methyl sulfate, formate acetate, proprionate citrate and tartarate.

2. Quaternary ammonium compounds in accordance with claim 1, in which $n_1$ and $n_2$ are numbers within the range from 0.5 to 2.

3. Quaternary ammonium compounds in accordance with claim 1, in which $R_1$ and $R_2$ have from about eight to about 14 carbon atoms.

4. Quaternary ammonium compounds in accordance with claim 1, in which $R_3$ and $R_4$ are methyl groups.

5. Quaternary ammonium compounds in accordance with claim 1, in which $R_1$ and $R_2$ are fatty alcohol alkyl groups derived from naturally-occurring fatty acids.

6. Quaternary ammonium compounds in accordance with claim 1, in which $R_1$ and $R_2$ are synthetic alcohol alkyl groups derived from the Oxo process.

* * * * *